United States Patent [19]
Webster

[11] 4,268,479
[45] May 19, 1981

[54] FLUID ANALYZER

[75] Inventor: Milo E. Webster, Braintree, Mass.

[73] Assignee: Instrumentation Laboratory Inc., Lexington, Mass.

[21] Appl. No.: 111,015

[22] Filed: Jan. 10, 1980

[51] Int. Cl.³ .............................................. G01N 1/10
[52] U.S. Cl. ...................................... 422/68; 73/425; 422/81; 422/103
[58] Field of Search .......................... 422/68, 81, 103; 73/421.5 R, 425; 141/130, 131

[56] References Cited
U.S. PATENT DOCUMENTS

| | | | |
|---|---|---|---|
| 862,045 | 7/1907 | Barnett . | |
| 1,992,485 | 2/1935 | Holmes . | |
| 2,206,816 | 7/1940 | Levitt | 422/103 |
| 2,494,774 | 1/1950 | Messick . | |
| 2,923,567 | 2/1960 | Jones et al. . | |
| 3,222,135 | 7/1965 | Ashmead | 422/103 |
| 3,362,228 | 1/1968 | Stuben | 422/103 |

OTHER PUBLICATIONS

IL540 Portable O₂ Analyzer Prod. Lit., Inst. Lab Inc., Sensor Lab. Div., 113 Hartwell Ave., Lexington, Ma. 02173, Aug. 1976.

Primary Examiner—Ronald Serwin

[57] ABSTRACT

A portable fluid analyzer has a sampling section with flow passage structure for sealing engagement with a discharge port of a zwickel fitting or the like and retainer structure for engagement with the fitting. The retainer structure is urged by a spring towards a retaining position and is movable, by a manual operator towards a released position. When the retainer structure is engaged with the fitting and the manual operator is released, the sealing member is urged by the spring into engagement with the fitting's discharge port. The analyzer also includes an analysis chamber connected to the discharge end of the flow passage structure and monitoring means for providing an output as a function of a constituent of the fluid in the analysis chamber.

12 Claims, 8 Drawing Figures

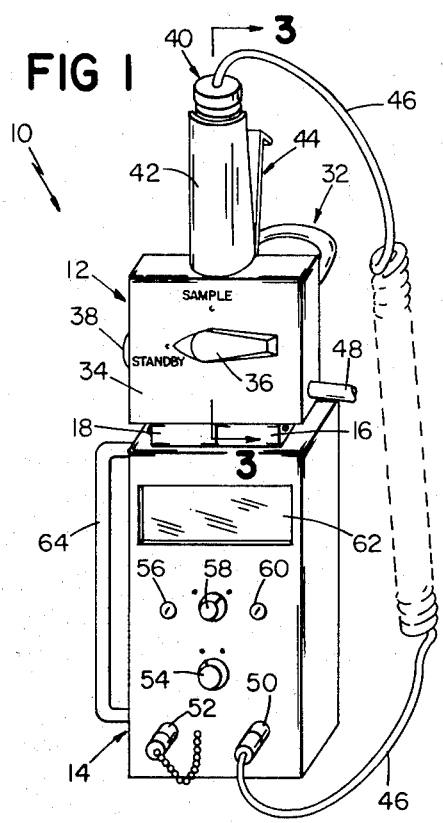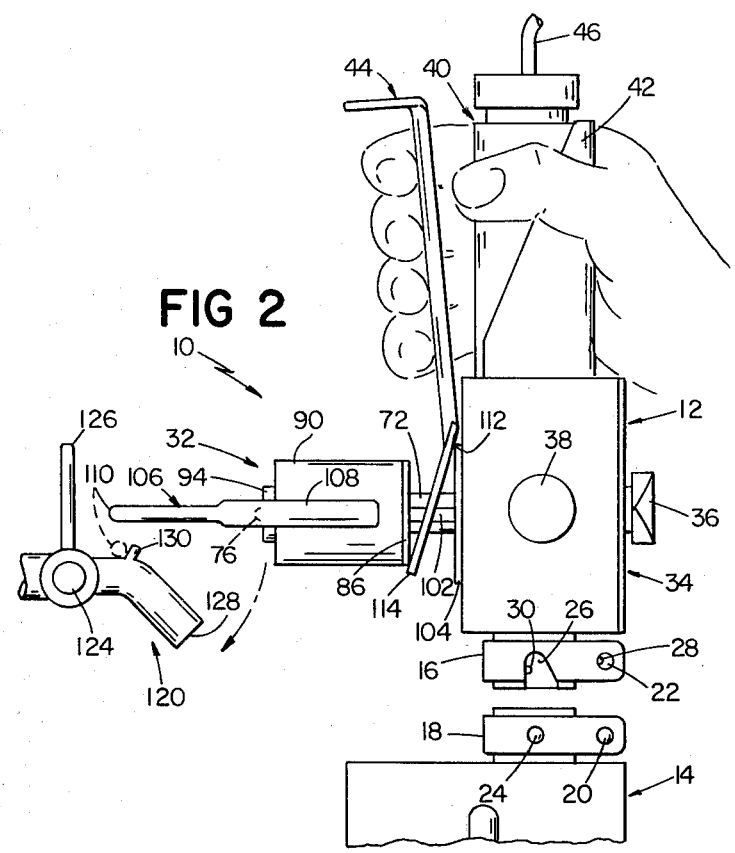

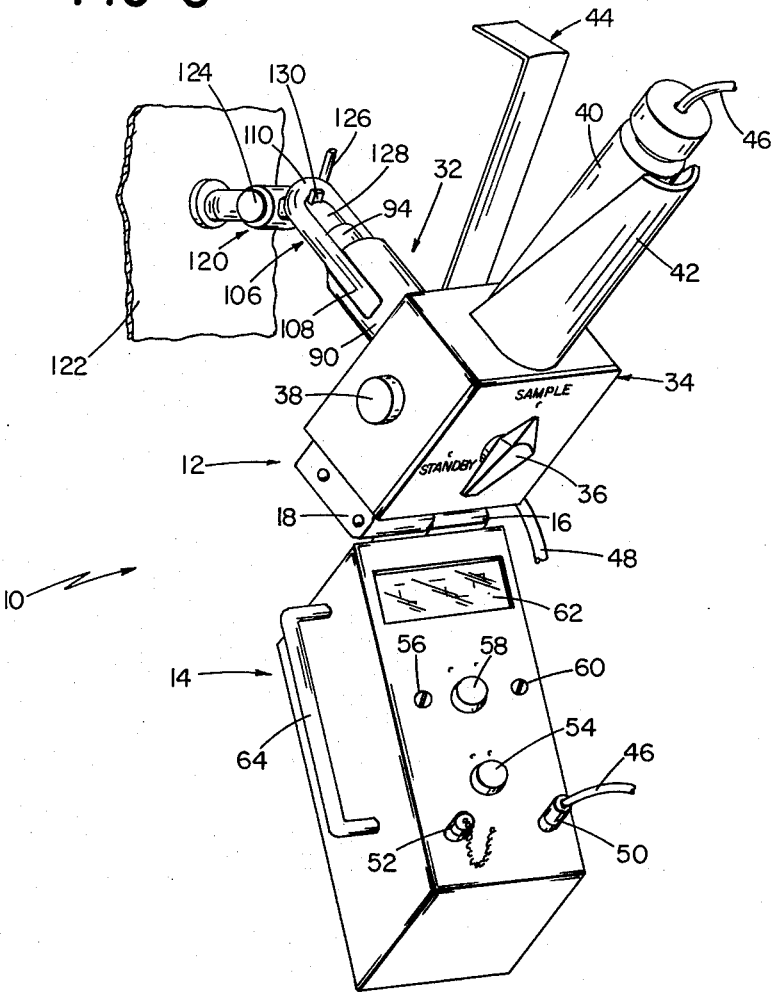

FLUID ANALYZER

This invention relates to portable fluid analyzers.

It is frequently desirable to monitor one or more constituents of a fluid at a number of different locations. For example, dissolved oxygen concentration in beer is a frequently measured parameter in the brewery industry. Oxygen at high concentration levels is required during the early stages of the brewery cycle, e.g., during the fermentation process. At later stages, however, oxygen is undesirable, especially in the final packaged product since it can adversely affect flavor quality and storage lifetime. There is a need for portable dissolved oxygen analyzers, with accuracies at the ppb level, which can be used for sampling not only the end product but also oxygen levels at other stages of the brewing process. Appropriate monitoring points in brewery installations are frequently located in cramped, or otherwise relatively inaccessible areas. In the past, such fluid sampling has required multiple component mechanisms and operation of those mechanisms has been relatively complex and tedious, for example involving the use of a zahm coupling (a screw type coupling) for attachment to a standard zwickel fitting.

In accordance with a feature of the invention, there is provided a portable fluid analyzer that has a sampling section comprising flow passage structure with a fluid inlet at one end thereof and a sealing member surrounding the fluid inlet for sealing engagement with a discharge port of a zwickel fitting or the like. Retainer structure for engagement with the fitting is urged by biasing means towards a retaining position and is movable, by manually operable means, towards a released position. When the retainer structure is engaged with the fitting and the manually operable means is released, the sealing member is urged by the biasing means into engagement with the fitting's discharge port. The analyzer also includes an analysis chamber connected to the discharge end of the flow passage structure and monitoring means for providing an output as a function of a constituent of the fluid in the analysis chamber.

In preferred embodiments, the flow passage structure includes a projecting guide surface for guiding entry of the fluid inlet into the discharge port of the cooperating fitting; and the retainer structure is mounted on a sleeve that slides along the axis of said flow passage structure between the retaining and released positions. A spring biases the sleeve towards the retaining position and opposed spaced handle and lever members, when urged towards one another in a one-handed operation, move the retainer structure towards its released position against the force of the spring for attachment to the fitting.

In accordance with another feature of the invention, disposed in fluid circuit between the flow passage structure and the analysis chamber is a valve which is movable between a sampling position and a standby position. The valve in the standby position provides a closed circuit that seals fluid in the analysis chamber and maintains pressure on the sensor in the analysis chamber, and also provides a flow passage directly between the fluid inlet and the drain. In the sampling position, the valve provides a flow path from the flow passage structure through the analysis chamber, and preferably through a flow control valve to a drain. The flow control valve is adjusted to preclude foaming of the liquid being analyzed during the sampling mode as foam tends to cause erratic readings. The analysis section is pivotably and detachably connected to the sampling section and includes a display of the measured constituent of the fluid to be analyzed. In a particular embodiment, the monitoring means is a polarographic electrode for measuring oxygen.

The invention provides a compact fluid analyzer with a sampling section that is easily and quickly attached to a cooperating fitting in a one-handed operation, even with fittings that are in inverted, cramped, or otherwise relatively inaccessible locations; and that is convenient in operation in providing fluid analyses in industrial and similar process applications.

Other features and advantages of the invention will be seen as the following description of a particular embodiment progresses, in conjunction with the drawings, in which:

FIG. 1 is a perspective view of a portable dissolved oxygen analyzer in accordance with the invention;

FIG. 2 is a side view of the analyzer shown in FIG. 1, with the analyzer section separated from the sampling section;

FIG. 3 is a sectional view taken along the line 3—3 of FIG. 1;

FIG. 4 is a sectional view taken along the line 4—4 of FIG. 3;

FIG. 5 is a perspective view of the analyzer in use;

FIG. 6 is a sectional view of the coupling of FIG. 5; and

FIGS. 7 and 8 are diagrams of the sampling valve in standby and sample positions respectively.

DESCRIPTION OF PARTICULAR EMBODIMENT

Shown in FIGS. 1 and 2 is a portable dissolved oxygen analyzer 10 that is specifically engineered for brewery applications and that includes a sampling section 12 and an analyzer section 14. Sections 12 and 14 are detachably attached in a pivot connection that includes coupling element 16 attached to sampling section 12 and coupling element 18 attached to analyzer section 14. Coupling element 18 carries pivot pin 20 and latch pin 24. Pivot pin 20 is received in pivot bore 22 of coupling element 16 attached to sampling section 12 and latch pin 24 is received in latch recess 26 in coupling element 16. Spring biased detents 28, 30 protrude into bore 22 and recess 26 respectively.

Sampling section 12, as shown in FIGS. 1 and 2, has coupling structure 32 for attachment to a standard zwickel fitting, housing 34 in which is disposed a control valve movable between a standby position and sampling position by control lever 36, a flow control valve controlled by knob 38, an oxygen sensor 40, and a pistol grip sampler mechanism that includes handle sleeve 42 and operating lever 44. Oxygen sensor 40 includes a polarographic oxygen sensor that is connected to analyzer section 14 by cable 46.

The analyzer section 14 includes a sensor receptacle 50 to which cable 46 is connected, charger receptacle 52, an on-off switch 54, a calibration control 56, a function control 58, a zero control 60, and a digital display 62. Analyzer section 14 may be carried by handle 64, either separately or attached to sampling section 12.

Details of the coupling structure 32 of sampling section 12 may be seen with reference to FIGS. 3 and 4. Secured to housing 34 is mounting block 70 into which is threadedly received conduit 72 that has a through passage 74 leading from spherical tip 76 to valve 78.

Received in a recess that surrounds spherical surface 76 is a resilient annular seal member 80. Carried on cylindrical body of conduit 72 is a slider 82 which had a seat 84 on which flange 86 of sleeve 90 is seated. Ring 92 is secured on head portion 94 of conduit 72 by snap ring 96. Helical spring 98, disposed between seat 100 of ring 92 and flange 86 of sleeve 90, urges slider 82 towards housing 34. Disposed between slider 82 and housing 34 is a resilient sheet spacer 104 and lever 44. Lever 44 has an elongated slot, is guided on conduit 72 by flats 102 (FIG. 2), and is seated on spacer sheet 104 by the action of spring 98 against slider 82, in the position shown in FIG. 3.

A coupling member 106 is formed of a U-shaped length of tubing with parallel flattened ends 108 which are welded to support sleeve 90 and an intermediate curved tubular coupling portion 110 that extends forward of and in alignment with tip 76.

The sampler unit 12 is quickly and easily attached to a zwickel fitting in a one-hand operation as shown in FIG. 2. The zwickel fitting 120 is attached to a vat 122 or other structure that contains the liquid to be analyzed and includes a valve structure 124 controlled by operating lever 126, a discharge port 128 to which the sampler unit inlet is to be attached, and an upstanding tang 130. In connecting sampler unit 12 to the zwickel fitting, the technician moves lever 44 towards housing handle 42 (as shown in FIG. 2). Lever 44 as it is moved towards handle 42 is pivoted about fulcrum 112 with its lower end 114 being moved outwardly away from housing 32 and moves slider 82 along shaft 72 sliding sleeve 90 along guide ring 92 to move coupling loop 110 outwardly away from coupling tip 76 in straight line movement and compressing spring 98. Loop 110 is placed over tang 130 and the sampling unit 12 is rotated downwardly and spherical guide surface 76 is inserted within the discharge port 128 of fitting 120. Lever 44 is then released. Spring 98 urges slider 82 and sleeve 90 rearwardly and loop 110 in engagement with tang 130 exerts sealing force between the discharge port 128 of the zwickel fitting 120 and seal 80 as shown in FIGS. 5 and 6. If the zwickel fitting is located in a cramped space, analysis section 14 may be detached from sampling section 12 as shown in FIG. 2.

Also mounted on block 70 is valve 78, further details of which may be seen with reference to the diagrams of FIGS. 7 and 8. Valve 78 has port 132 connected to passage 74, a second port 134 connected to oxygen sampling cuvette 136 of the polarographic oxygen sensor 40, a third port 138 connected to the other end of cuvette 136 through flow control valve 140, and a fourth port 142 connected to drain 48. A movable valve member 144 has passages 146 and 148. Valve member 144 is moved between a standby position (shown in FIG. 7) and a sample position (shown in FIG. 8) by control handle 36. In the standby position (FIG. 7), inlet conduit 72 is connected to drain 48 through valve passage 146, and cuvette 136 is connected in closed circuit by the valve passage 148. When valve lever 36 is rotated 90 degrees to the sample position (FIG. 8), fluid flow passage 146 connects inlet conduit 72 to the inlet of oxygen cuvette 136, and valve passage 148 connects the outlet of oxygen cuvette 136 through flow control valve 140 to drain 48.

In operation, with the sampling valve 78 in standby position, the pistol grip lever 44 is squeezed and the U-shaped yoke 110 is positioned over tang 130 of the zwickel fitting. The lever is released and spring 98 urges the spherical aligning surface 76 into the discharge port 128 of the zwickel fitting and seats that port against seal 80. The zwickel valve 120 is then opened (by lever 126) and the sample liquid is allowed to flow to drain for five seconds to eliminate air from the system. The sampling valve 78 is then turned to sample position (FIG. 8) and the flow rate is adjusted by control knob 38 to obtain a steady flow of the liquid to be analyzed from discharge tube 48, without foaming in sensor cuvette 136 (a typical flow rate being about two gallons per hour). The sample to be analyzed is directed into cuvette 136 where it is exposed to the membrane surface of oxygen sensor 40. This membrane is gas permeable and oxygen diffuses into the sensor where it is exposed to an electrode maintained at a voltage at which only oxygen is reduced. The resulting reduction reaction produces a signal that is directly proportional to the oxygen concentration in the sample. This signal is conditioned, amplified, and displayed on the digital panel meter 62 which reads directly in ppb dissolved oxygen. After the reading has been taken, the sampling valve 78 is returned to standby position, the zwickel valve 124 is closed and the instrument is disconnected from the zwickel fitting by pressing pistol grip lever 44 and lifting coupling 110 off tang 130.

While a particular embodiment of the invention has been shown and described, various modifications will be apparent to those skilled in the art and therefore it is not intended that the invention be limited to the disclosed embodiment or to details thereof and departures may be made therefrom within the spirit and scope of the invention.

What is claimed is:

1. A portable fluid analyzer for attachment to a zwickel fitting or the like comprising
   a sampling section comprising flow passage structure having a fluid inlet at one end thereof, a sealing surface carried by said flow passage structure for sealing engagement with a discharge port of the fitting,
   retainer structure for engagement with said fitting, said retainer structure being movable between a retaining position, and a released position spaced further from said fluid inlet then said retaining position,
   biasing means for urging said retainer structure towards said retaining position,
   spaced handle and lever portions that are manually movable towards one another for moving said retainer structure towards said released position,
   an analysis chamber connected to said flow passage structure,
   monitoring means in monitoring relation to said analysis chamber for providing an output as a function of a constituent of the fluid to be analyzed, and
   an analysis section for processing the output of said monitoring means and producing an output.

2. A portable fluid analyzer for attachment to a zwickel fitting or the like comprising
   a sampling section comprising flow passage structure having a fluid inlet at one end thereof, a sealing surface carried by said flow passage structure for sealing engagement with a discharge port of the fitting,
   attachment structure for attaching said sampling section to said fitting,
   an analysis chamber connected to said flow passage structure, a valve disposed between said flow passage structure and said analysis chamber, said valve being movable between a sample position and a standby position, said valve in said sample position providing a series flow path from said flow passage structure through said analysis chamber to a drain, and in said standby position providing a flow path directly from said flow passage structure to said drain and a separate closed circuit for sealing fluid in said analysis chamber, monitoring means in monitoring relation to said analysis chamber for providing an output as a function of a constituent of the fluid to be analyzed, and an analysis section for processing the output of said monitoring means and producing an output.

3. The analyzer of either claim 1 or 2 wherein said sampling section includes a projecting guide surface adjacent said fluid inlet for guiding said fluid inlet into sealing engagement with a discharge port of the fitting.

4. The analyzer of either claim 1 or 2 and further including a detachable connection between said sampling and analysis sections.

5. The analyzer of claim 4 wherein said detachable connection includes a pivot connector and latch means for fixing said pivot connector in a predetermined position so that said sampling and analysis sections are in predetermined relation to one another.

6. The analyzer of claim 1 wherein said sampling section further includes a valve disposed between said flow passage structure and said analysis chamber, said valve being movable between a sample position and a standby position, said valve in said sample position providing a series flow path from said flow passage structure through said analysis chamber to a drain, and in said standby position providing a flow path directly from said flow passage structure to said drain and a separate closed circuit for sealing fluid in said analysis chamber.

7. The analyzer of either claim 2 or 6 and further including a flow control valve that is connected in said series flow path when said valve is in said sample position.

8. The analyzer of either claim 1 or 2 wherein said retainer structure is slidably mounted on said flow passage structure and said retainer structure includes a retainer surface located forward of said fluid inlet in both said retaining and released positions, said retainer surface being closer to said fluid inlet in said retaining position than in said released position.

9. The analyzer of claim 1 wherein said polarographic electrode has an elongated body portion, said handle portion is fixed in overlying protective relation relative to said body portion, and said lever portion is coupled to said retainer structure for sliding said sleeve member along said flow passage structure in response to movement of said lever portion towards said handle portion for moving said retainer structure toward said released position.

10. The analyzer of either claim 1 or 6 wherein said retainer structure includes a sleeve member slidably mounted on said flow passage structure and a loop portion secured to said sleeve member, and said biasing means is a helical spring disposed between said flow passage structure and said sleeve member for urging said sleeve member along said flow passage structure away from said fluid inlet.

11. The analyzer of claim 10 wherein said monitoring means is a polarographic electrode for measuring oxygen and said analysis section included a digital display for indicating the amount of oxygen in the fluid being analyzed as sensed by said polarographic electrode.

12. The analyzer of claim 11 further including a detachable pivot connector between said sampling and analysis sections and latch means for fixing said pivot connector in a predetermined position so that said sampling and analysis sections are in predetermined relation to one another.

* * * * *